(12) United States Patent
Appling

(10) Patent No.: US 6,283,950 B1
(45) Date of Patent: *Sep. 4, 2001

(54) OCCLUDING WIRE ASSEMBLY

(75) Inventor: William M. Appling, Hartford, NY (US)

(73) Assignee: AngioDynamics, Inc., Queensbury, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,640

(22) Filed: Jun. 11, 1998

(51) Int. Cl.[7] .................................................. A61M 25/01
(52) U.S. Cl. ........................ 604/528; 604/264; 604/246; 604/249; 604/523; 600/585
(58) Field of Search .................... 604/167, 164, 604/246, 249, 264, 523, 528, 533, 534, 525, 537, 247, 256, 236, 167.01, 167.03, 164.01, 164.02, 164.13; 600/585; 251/149, 149.1

(56) References Cited

U.S. PATENT DOCUMENTS

| | | | |
|---|---|---|---|
| Re. 34,633 | * 6/1994 | Sos et al. ........................... | 128/772 |
| 4,512,766 | 4/1985 | Vailancourt . | |
| 4,559,046 | * 12/1985 | Groshong et al. ................... | 604/282 |
| 4,846,174 | * 7/1989 | Willard et al. ....................... | 128/344 |
| 4,875,481 | * 10/1989 | Higgins ................................ | 128/344 |
| 4,940,062 | * 7/1990 | Hampton et al. .................... | 128/772 |
| 5,167,239 | * 12/1992 | Cohen et al. ......................... | 128/772 |
| 5,192,295 | * 3/1993 | Danforth et al. ..................... | 606/194 |
| 5,207,229 | * 5/1993 | Winters ................................ | 168/772 |
| 5,242,430 | * 9/1993 | Arenas et al. ........................ | 604/280 |
| 5,246,009 | * 9/1993 | Adams ................................. | 128/772 |
| 5,250,034 | 10/1993 | Appling et al. . | |
| 5,273,052 | * 12/1993 | Kraus et al. .......................... | 128/772 |
| 5,304,198 | * 4/1994 | Samson ................................ | 606/194 |
| 5,437,632 | * 8/1995 | Engelson .............................. | 604/53 |
| 5,465,733 | * 11/1995 | Hinohara et al. .................... | 128/772 |
| 5,505,699 | * 4/1996 | Forman et al. ....................... | 604/96 |
| 5,624,396 | * 4/1997 | McNamara et al. ................. | 604/93 |
| 5,906,606 | * 5/1999 | Chee et al. ........................... | 604/527 |
| 6,017,323 | * 1/2000 | Chee ..................................... | 604/96 |
| 6,027,461 | * 2/2000 | Walker et al. ........................ | 600/585 |

FOREIGN PATENT DOCUMENTS

| | | |
|---|---|---|
| 3326648 | 2/1985 | (DE) . |
| 0827759 | 3/1998 | (EP) . |
| 8904686 | 6/1989 | (WO) . |

* cited by examiner

*Primary Examiner*—Richard K. Seidel
*Assistant Examiner*—Cris Rodriguez
(74) *Attorney, Agent, or Firm*—Reed Smith LLP

(57) ABSTRACT

A catheter assembly for introducing material into the vascular system has an elongated catheter body forming a lumen with a hole at its distal end thereof, a catheter hub positioned at the proximal end of the catheter body and an occluding wire hub detachably connected with the catheter hub. The occluding wire hub has a cavity and an opening therethrough for communication with the lumen in order to provide for the introduction of infusion fluid into the lumen. An occluding wire, having a proximal end and a distal end, is positioned so that it extends from the occluding wire hub through the catheter hub and the lumen. The distal end of the occluding wire has an occluding region adapted to engage the distal end hole. The proximal end of the occluding wire terminates within the occluding wire hub and has an anchor positioned within the hub cavity to prevent removal of the wire from the occluding wire hub when the occluding wire hub is disconnected and removed from the catheter body. The anchor, which is contained within the hub cavity, is movable between a proximal position and a distal position within the cavity. A compression spring has a distal end fixed to the occluding wire and a proximal end positioned within said occluding wire hub to thereby urge the wire in the distal direction into an occluding position.

6 Claims, 5 Drawing Sheets

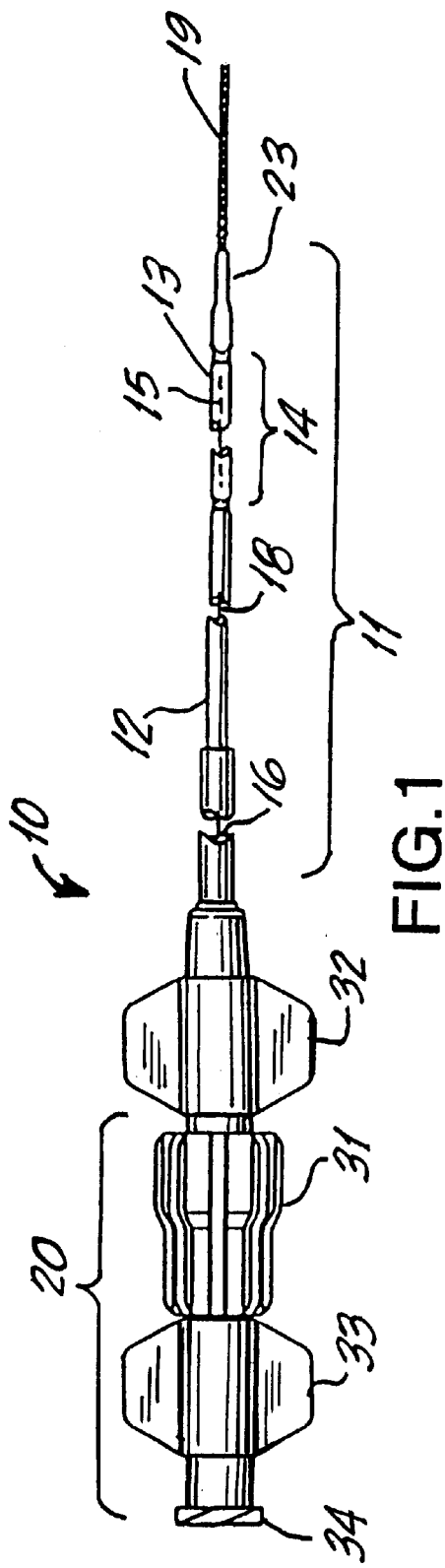
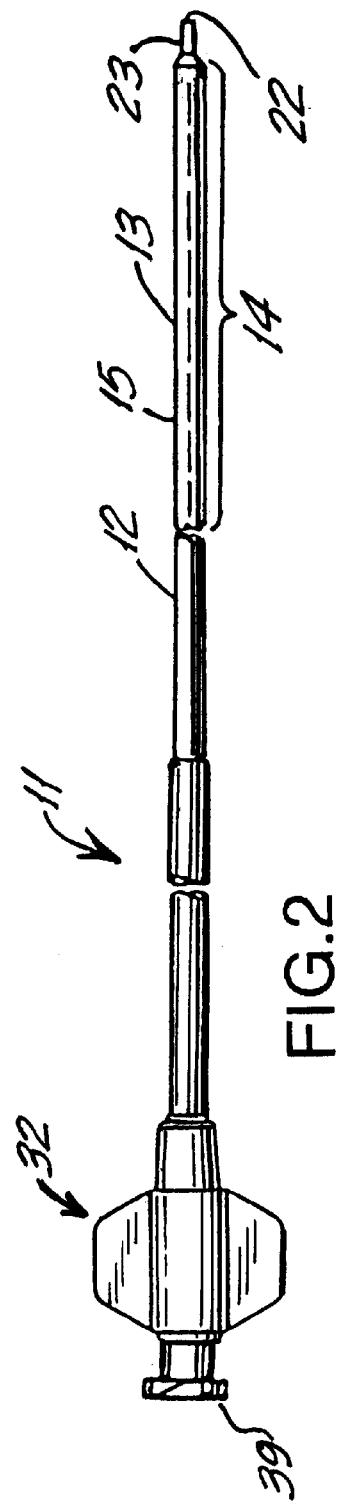
FIG.1
FIG.2

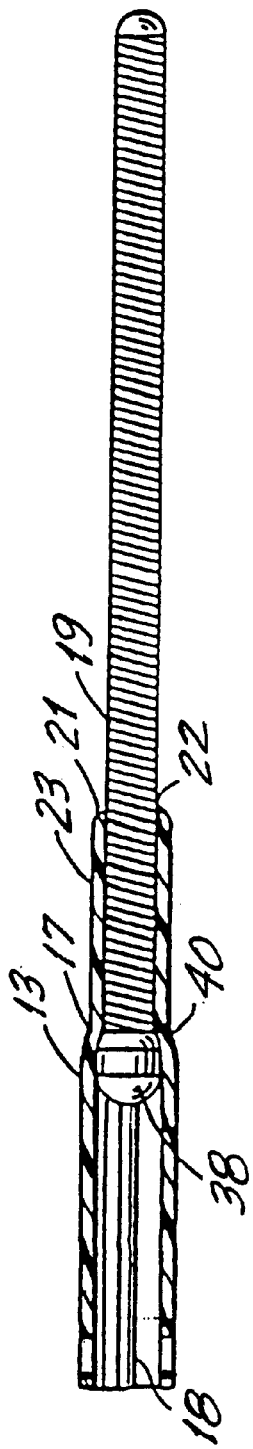
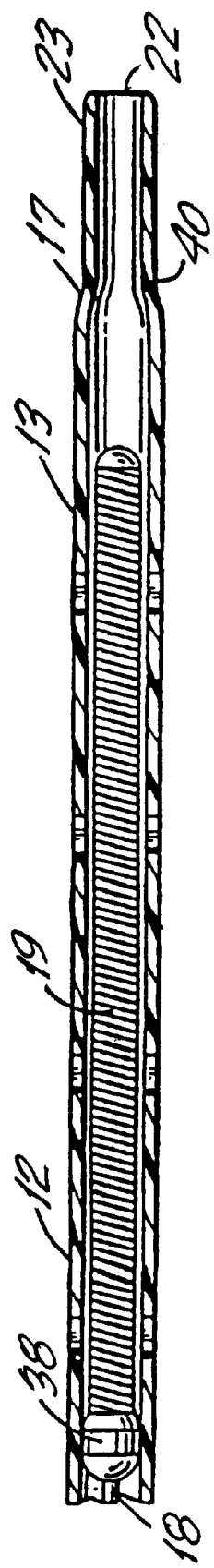
FIG.3
FIG.4

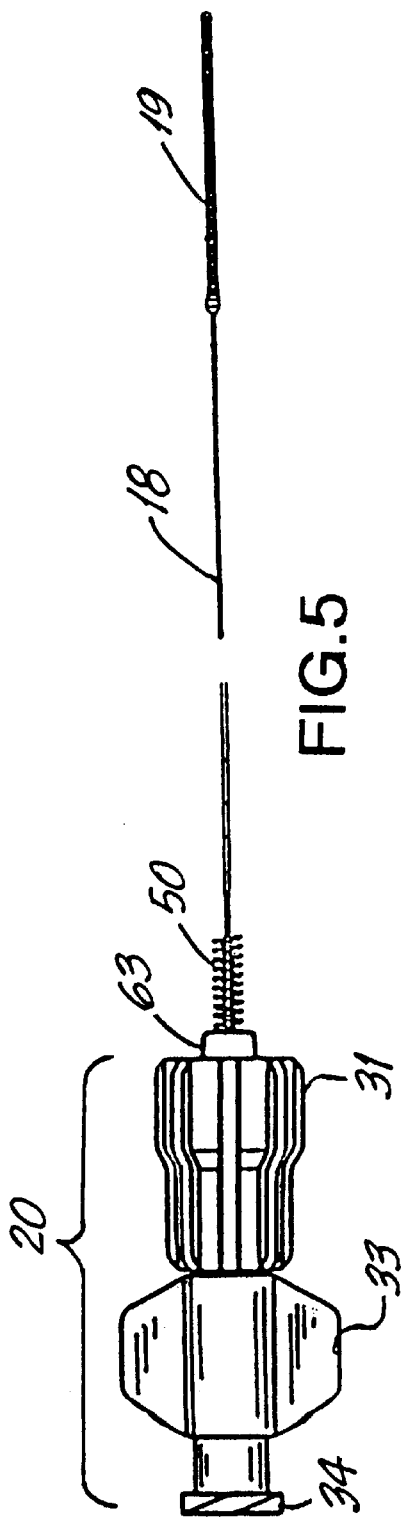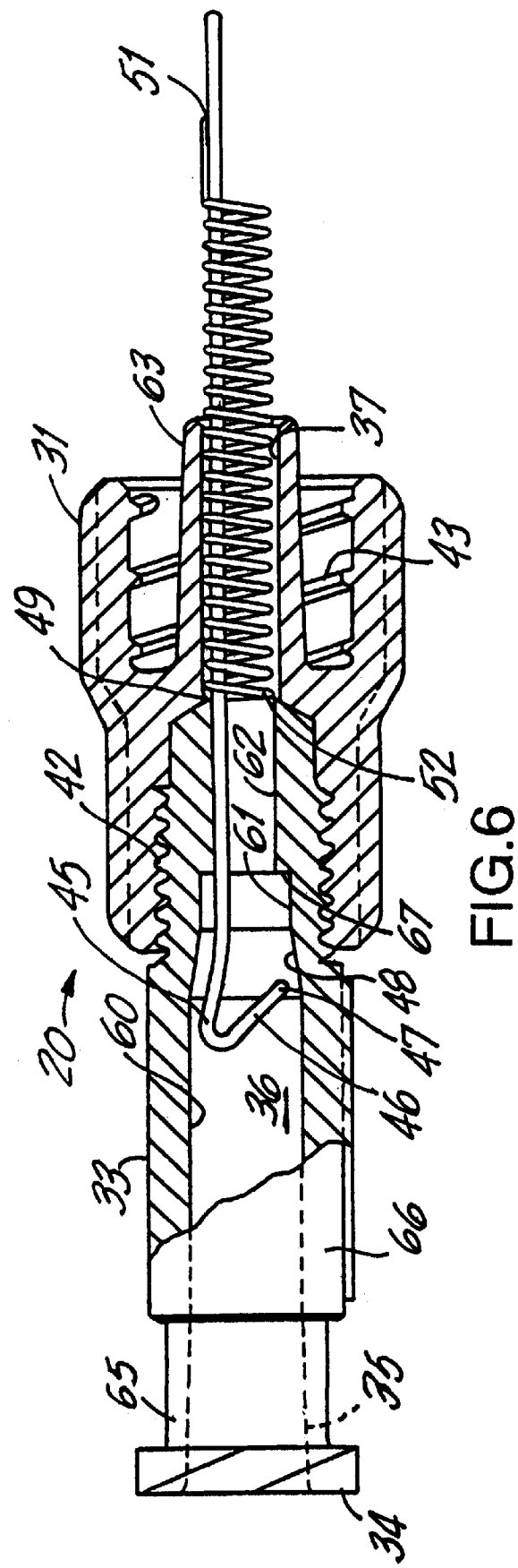

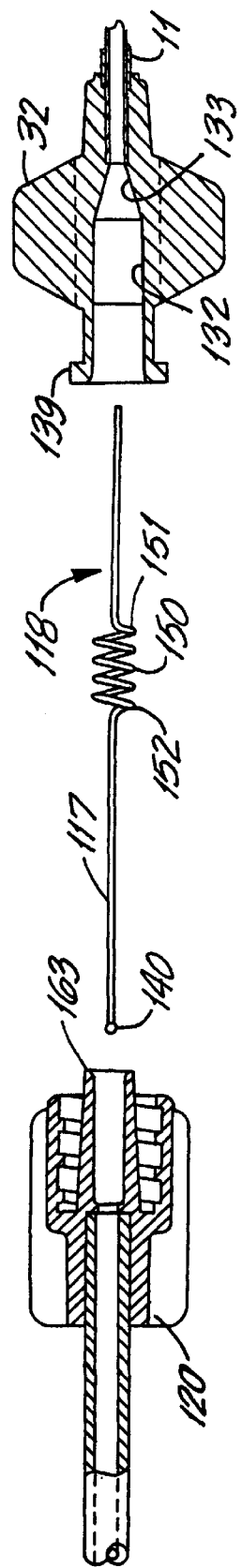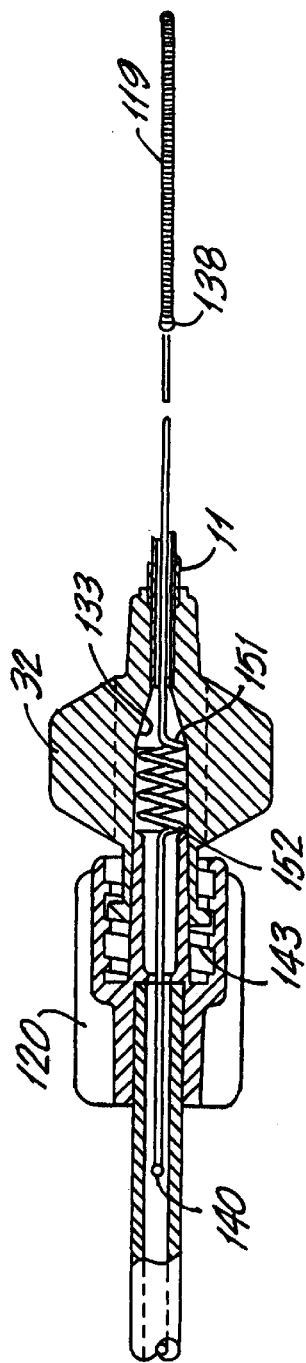

OCCLUDING WIRE ASSEMBLY

FIELD OF THE INVENTION

The present invention relates generally to the field of catheters for use in delivering material into the vascular system, and more particularly, to such a catheter having an occluding wire which terminates in a proximal wire hub. Means may be provided for automatically adjusting the position of the occluding wire within the catheter body.

BACKGROUND OF THE INVENTION

Catheters which are used to infuse fluids into a vascular system and which incorporate occluding wires are well known in the art. Typically, such a catheter has an elongated body with proximal and distal ends. A catheter lumen is formed interiorly of the body. A hole or opening is located at the distal end of the body so that fluid can pass from the catheter lumen through the hole into the vascular system. This opening also provides a passageway through which a guide wire can fit. Fluid material intended to be delivered to the vascular system is introduced into the catheter lumen through its proximal end. Pressure responsive exits in the form of slits may be arranged in a side wall of the catheter body as a means for infusing the fluid material from the catheter lumen into the vascular system at a desired rate and location. Occluding wires are typically arranged so that they extend longitudinally within the lumen and fit into the opening in the distal end blocking fluid from exiting the end hole. The opening therefore serves as another means for passage of fluid from the catheter lumen into the vascular system depending on the position of the occluding wire. When the occluding wire is in the occluded position, the distal end hole will be closed and fluid will pass through the slits. If the occluding wire is removed from the catheter lumen, then fluid will pass through the end hole. When infusing fluid into the vascular system through such a catheter, it is necessary to have a fitting or other structure connected to the catheter, at its proximal end, in order to provide a means for introducing the fluid material into the catheter lumen and to secure the occluding wire in place during infusion procedures. A common type of fitting or structure used for this purpose is a hemostasis y-adapter. An example of a hemostasis y-adapter as a means to secure an occluding wire is marketed by AngioDynamics, Incorporated, under the brand name of "Pulse*Spray®". The AngioDynamics® Pulse*Spray® Infusion System utilizes a hemostasis y-adapter with a Touhy Borst valve on the adapter's through lumen proximal end. The Touhy Borst valve provides a means to open and allow a guide wire to be inserted or withdrawn, or closed to provide a seal and retention mechanism around a guide wire. A rotating male luer fitting is attached to the distal end of the through lumen. This distal male luer fitting allows removable attachment to the catheter's proximal female luer fitting. A second side lumen intersects the through lumen of the adapter at an acute angle. The side lumen ends with a female luer fitting having a port to allow fluid to be injected into the y-adapter. The proximal end of the occluding wire passes through the through lumen of the y-adapter and extends through the Touhy Borst valve opening beyond its proximal end. The Touhy Borst valve incorporates a rotating cap which can be turned to open or close the valve around the occluding wire's proximal shaft. When such a catheter is in use, the occluding wire may be caused to move out of its desired occluding position, either as a result of some tortuous path experienced during catheter insertion, or it may be moved as a result of its engaging the inner walls of the catheter lumen during possible bending of the catheter. Therefore, the user may be required to manually adjust the position of the wire to insure its occluding function. Such an adjustment is a time-consuming and difficult maneuver to accomplish while trying to accurately place the catheter into a proper position within a patient to infuse fluid into the vascular system.

Y-adapters of the type discussed above are large and bulky. In prior known adapters, the fitting can have a length of several inches, thus they are difficult to handle in complicated catheter insertion procedures. In addition, such adapters are expensive and add cost to catheterization procedures. Another disadvantage of using y-adapters involves priming procedures. Prior to using any catheter, its lumen system must be primed in order to remove any air from the catheter as well as from any lumens or passages in an adapter to which the catheter is connected. Priming a catheter which has a y-adapter can be difficult in view of the fact that y-adapters involve multi-lumen configurations. Priming a y-adapter to be coupled to a catheter involves many steps and begins prior to connecting the adapter to the catheter. First, a normal heparinized saline must be slowly introduced through the side lumen by a syringe which is inserted into the side port. This continues until the saline drips out of its through port. The distal fitting of the y-adapter is attached to the catheter while more saline is pumped into the system, purging air from the Touhy Borst valve. The occluding wire can now be inserted through the Touhy Borst valve and into the catheter lumen. The occluding wire is advanced until the occluding ball seats into the catheter's tapered tip. While maintaining positive pressure on the syringe to prevent air from entering the adapter's lumen and pushing forward on the occluding wire to insure placement of the ball against the seat, the Touhy Borst valve is closed. Therapeutic fluid may now be introduced into the large volume occupied by the two lumens and passages of the y-adapter. This is a complicated and time-consuming process. In addition, this procedure requires large amounts of both saline and therapeutic fluids to complete the priming process, thus adding more cost to the catheterization procedure.

Because the occluding wire passes through the Touhy Borst valve and is thus exposed, there is the added risk that either a patient or medical personnel may inadvertently manipulate the proximal end of the wire which extends beyond the proximal end of the hemostasis y-adapter. Such inadvertent manipulation could result in ineffective occluding function of the wire, thus reducing effectiveness of the catheter during infusion procedures. Exposure of the wire beyond the y-adapter proximal end also increases possibilities of infection, as it is difficult to maintain a sterile condition of the wire.

Other difficulties with the prior art arrangements involve the need to be able to longitudinally adjust the position of the occluding wire during the catheter procedure due to the fact that the catheter may bend as it passes through tortuous pathways and the occluding wire may come into contact with the inner surfaces of the catheter side walls, thus resulting in variations in the length of engagement of the wire in the passageways. In order to compensate for this movement of the wire, it is frequently necessary to manually adjust the position of the wire in order to maintain full occluding of the hole at the catheter distal end. In order to achieve such manual adjustment, it may be necessary for the operator to conduct the adjustments by holding the y-adapter while simultaneously opening the Touhy Borst valve, adjusting the location of the wire, purging air from the y-adapter's lumen, and then retightening the valve, while maintaining sterility of all components. Improper adjustment could result in inefficient or failure of infusion of fluid into the vascular system, or could result in misalignment of the catheter in the vascular passages.

OBJECTS OF THE INVENTION

It is accordingly a general object of the present invention to provide a catheter assembly with an occluding wire that overcomes the foregoing disadvantages.

It is a specific object of the invention to provide a catheter assembly having a catheter body and an occluding wire hub with a single lumen, the hub being coupled to the catheter body at its proximal end, with the hub being coaxially aligned with and in fluid communication with the lumen of the catheter, such assembly having an occluding wire which extends from the occluding wire hub, through its lumen and into the catheter body. In this manner, the occluding wire is contained wholly within the assembly of catheter and its associated hub.

Yet another object of the present invention is to provide a catheter having a self-adjusting occluding wire in which a compression spring is integral with or connected to the occluding wire to urge the wire in a distal direction in order to constantly insure that the wire is in a proper occluding position without the need for manual adjustments.

A still further object of the invention is to provide an anchor at the proximal end of the occluding wire so that it may be movable between proximal and distal positions within the through lumen of the hub in order to accommodate assembly of the hub with catheter bodies having different lengths but which are within specified manufacturing tolerances.

Yet another object of the present invention is to provide a catheter assembly in which an occluding wire is positioned in the lumen of the catheter body and is connected to a wire hub which is coupled to the catheter proximal end in order to eliminate the use of complex y-adapter type fittings, thus simplifying catheter procedures.

Another object of the present invention is to provide a catheter assembly in which the occluding wire is wholly contained within the structure of the catheter assembly, thus minimizing any risk of infection or inadvertent manipulation.

A further object is to provide a catheter assembly having a catheter body with a proximal catheter hub, a wire hub detachably connected to the catheter hub, and an occluding wire carried by the wire hub in such a manner as to prevent removal of the occluding wire from the wire hub when it is disconnected from the catheter hub.

Still another object of the invention is to provide a catheter assembly in which the luer fitting adapter has only a single lumen, thus simplifying priming procedures and minimizing the amount of therapeutic fluid required during priming.

Another purpose of the invention is to provide a catheter assembly having an occluding wire at lower cost than heretofore available.

BRIEF DESCRIPTION

The invention is directed to a catheter assembly for introducing material into the vascular system which has an elongated catheter body forming a lumen and having a hole at the distal end thereof A catheter hub is assembled with the catheter body at the catheter body proximal end. A wire hub is detachably connected with the proximal end of the catheter hub. The wire hub has a cavity therein and an opening for communication with the catheter hub and catheter body lumen in order to provide means for introduction of infusion fluid into the catheter lumen. An occluding wire, having a proximal end and a distal end, is positioned so that it extends from the wire hub through the catheter hub and the lumen. The distal end of the occluding wire has an occluding region adapted to engage the distal end hole. The proximal end of the occluding wire is positioned within the hub cavity. An anchor is carried at the proximal end of the wire to insure its position within the hub.

A further feature is the provision of a compression spring having a distal end fixed to the occluding wire with its proximal end positioned within the wire hub so that it may expand and contract in a longitudinal direction which is parallel to the axis of the occluding wire. The anchor, which is contained within the cavity of the wire hub, is movable between a proximal position and a distal position within the cavity. The spring tends to urge the wire in the distal direction, thus providing automatic means for adjusting the position of the wire. The anchor provides a means for retaining the occluding wire within the wire hub. When the occluding wire is removed from the catheter's lumen by grasping and moving the hub proximally away from the catheter body, the anchor will come into contact with a shoulder in the cavity of the hub causing high force to be applied in tensile to remove the wire without possible damage to the compression spring.

The foregoing and other features of the present invention are more fully described with reference to the following drawings annexed hereto.

BRIEF DESCRIPTION OF THE DRAWINGS

FIG. 1 is a side elevational view of the catheter assembly of the present invention;

FIG. 2 is a side elevational view of the catheter body portion and catheter hub of the catheter assembly shown in FIG. 1;

FIG. 3 is an enlarged sectional view illustrating the distal end of an occluding wire located in the catheter distal end with its end hole sealed;

FIG. 4 is a view similar to FIG. 3 showing the distal end of the occluding wire in a position in which the end hole is open;

FIG. 5 is a side elevational view showing the occluding wire assembled with the compression spring and supported within the proximal hub;

FIG. 6 is an enlarged cross-sectional view illustrating one embodiment of the hub with the anchor positioned within the cavity of the hub;

FIG. 8 is a sectional view illustrating a further embodiment of a catheter assembly with an occluding wire; and FIG. 9 is an exploded sectional view showing the assembly illustrated in FIG. 8.

DESCRIPTION OF THE PREFERRED EMBODIMENT

Figure 7:
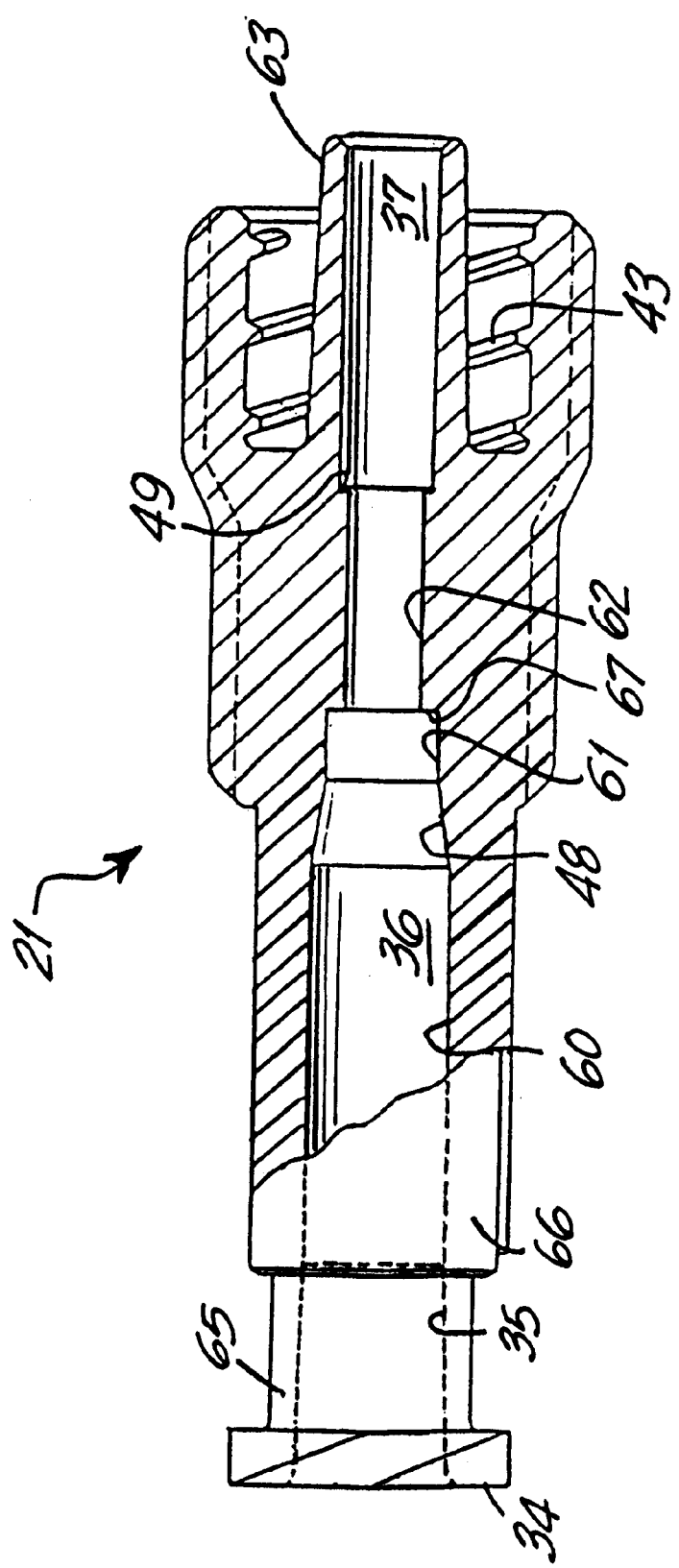
FIG. 7 is an enlarged cross-sectional view illustrating an alternative embodiment of the proximal hub.

Referring to the drawings and with particular reference to FIG. 1, reference numeral 10 denotes the catheter assembly of the present invention for delivering therapeutic or diagnostic fluid into a vascular system. The catheter assembly 10 includes an elongated catheter body portion 11, a proximal catheter hub portion 32 (sometimes referred to as a female luer fitting adapter) which is assembled with the catheter body portion 11, and an occluding wire hub 20. Hub 20 is coupled at its distal end to catheter hub portion 32 in a manner described below to permit hub 20 to be detached from catheter hub 32. Catheter body portion 11, which is illustrated together with proximal catheter hub 32 in FIG. 2, has an annular side wall 12 defining interiorally thereof a catheter lumen 16. Catheter body 11 has a distal portion 13 which includes an infusion section 14. Infusion section 14 is provided with a plurality of slits 15 which serve as pressure valves for infusion purposes as described more fully in U.S. Pat. No. 5,250,034. The catheter assembly 10 also includes an occluding wire 18 carried by occluding wire hub 20 and extending longitudinally within the lumen 16 of catheter body 11. The proximal end of wire 18 extends into and is supported by the proximal wire hub 20. Occluding wire 18 may have a coil spring 19 at its distal end which is intended to protrude beyond the catheter distal end as illustrated in FIG. 1 and as more fully appreciated and described below with reference to FIG. 3. Because the catheter body is intended to be moved through a vascular pathway which may not be straight, it is usually made of a material that will allow it to flex and bend.

With particular reference to FIGS. 2, 3 and 4, the distal portion 13 of the catheter body 11 includes tapered zone 17. The tapered zone 17 forms a seat 40 for an occluding ball 38 carried by the wire 18. Positioned distally of the tapered zone 17 is a straight portion 23 terminating in end 21 through which there is a distal end hole 22. When the wire is positioned distally within the catheter, occluding ball 38 will seat within the tapered zone 17 and coil spring 19 will pass through end hole 22 in order to seal the distal end hole 22. As a result of sealing end hole 22, fluid will be prevented from flowing through the distal end hole 22 and all fluid flow will be through the slits 15. When it is desired to direct the fluid through end hole 22 without infusion through the slits 15, wire hub 20, with the occluding wire connected to it, may be uncoupled and detached from catheter body 11 and the wire 18 withdrawn from catheter body 11. In this manner, catheter body 11 will, as illustrated in FIG. 2, be left without the wire while the catheter body 11 will remain in place in a vascular passage. Without the occluding wire proximal hub 20 coupled to the catheter hub 32, fluid will be introduced to the catheter directly by attaching a syringe to the female luer fitting 39 located on the catheter hub 32. Female luer fitting 39 is part of catheter proximal hub 32 and communicates directly with lumen 16. FIG. 4 illustrates occluding wire 18 as it is retracted toward the proximal end of the catheter, thus causing ball 38 to unseat from seat 40, permitting fluid to flow through the end hole 22. The withdrawn occluding wire assembled with its wire hub 20 is illustrated in FIG. 5.

In one embodiment, occluding wire hub 20 has a hub fitting 31. Hub fitting 31 is assembled at its distal end with catheter hub portion 32 which is located at the proximal end of the elongated catheter body portion 11. The proximal end of hub fitting 31 is assembled with the distal end of a luer fitting 33. Luer fitting 33 has a luer adapter 34 at its proximal end. Luer adapter 34 is arranged to receive a syringe or other means for injection of fluid through an opening (not shown).

With reference now to FIG. 6, luer adapter 34 communicates through passageway 35 in extension 65 of luer fitting 33 with a cavity 36 formed in the main body portion 66, which in turn communicates with lumen 37 in hub fitting 31. When luer fitting 33 is assembled with hub fitting 31 passageway 35 is in direct communication with lumen 37 through the cavity 36. In turn, when hub fitting 31 is assembled with proximal catheter hub 32 of catheter body 11, lumen 37 will be in fluid communication with lumen 16. In this manner, fluid injected at luer adapter 34 will pass along a continuous fluid path through fittings 33 and 31 into lumen 16 so that it may be infused through the slits in annular side wall 12 of catheter body 11 or through end hole 22 into the vascular system. Luer fitting 33 is coupled with hub fitting 31 through the use of a threaded connection 42. Adhesive is applied to the threaded connection 42 to prevent leaks and disconnection after manufacturing. Other means of connection may be envisioned. Threads 43 at the distal end of hub fitting 31 are provided to interact with port adapter 39 on catheter fitting 32 to provide an appropriate means for coupling. Male luer taper core 63, the interior of which forms lumen 37, extends distally through the area of threads 43. When the wire hub 20 is assembled with catheter proximal hub 32 of the catheter body 11 core 63 will be inserted into a female opening (not shown) in port adapter 39 to establish the communication between lumen 37 of hub 20 and lumen 16 of catheter body 11. A fluid path is thus established from luer adapter 34 through the fittings 33, 31 and catheter hub 32 as a result of communication among passageways 35, cavity 36, lumen 37 and lumen 16.

An alternative embodiment of proximal hub 20 is illustrated in FIG. 7. In this embodiment luer fitting 33 and hub fitting 31 would be constructed as a unitary hub member 41 so that no assembly of luer fitting 33 and hub fitting 31 would be required.

When the occluding wire hub 20 is assembled with catheter hub 32, their respective longitudinal axes are coaxially aligned, and the occluding wire 18 is fully contained within the fluid path. No portion of occluding wire 18 will extend beyond the proximal end of the catheter assembly 10. Rather, the proximal end of occluding wire 18 terminates with a hook shaped anchor 45. Anchor 45 is preferably integrally formed with the longitudinal body or shaft of wire 18. Anchor 45 has a return portion 46 with its end 47 facing the distal direction. Cavity 36 has an enlarged diameter section 60 and a tapered section 48. On the distal side of tapered section 48 cavity 36 has a first reduced diameter section 61 and a second reduced diameter section 62. Section 62 communicates with lumen 37. A shoulder 67 is located in fitting 33 at the transition between reduced diameter sections 62 and 61. Anchor 45 is arranged so that it is free-floating within section 60 of the cavity 36. The distal movement of anchor 45 and thus wire 18 is limited by the end 47 of return portion 46 engaging tapered wall surface 48 of the cavity 36 and ultimately shoulder 67. All distal movement of wire 18 will positively stop when the anchor end 47 engages shoulder 67. In a preferred embodiment, the axial length of sections 60, 48 and 61 of cavity 36 is between 0.5 and 1.0 inches and is preferably 0.875 inches. The inside diameter of section 60 is about 0.155 inches. Tapered wall surface 48 extends a distance of approximately 0.10 inches along a direction parallel to the longitudinal axis. Anchor 45 can move within sections 60 and 48 of cavity 36 between fully distal and fully proximal positions a distance of between about 0.25 inches and 0.75 inches but preferably a distance of 0.59 inches.

A compression spring 50 is located in lumen 37 of occluding wire hub 20. The distal end 51 of compression spring 50 is welded, soldered or otherwise connected to occluding wire 18 at a position distally beyond the distal end of core 63. Proximal end 52 of the compression spring 50 abuts against shoulder 49 located on the distal end of luer fitting 33 at the transition of section 62 and lumen 37.

Compression spring 50 can expand and contract in a direction parallel to the axis of the hub 20 and distally urges occluding wire 18 into its occluding position in order to insure proper seating of occluding wire ball 38 into the tapered surface 17 forming its seat 40 and to thus close end hole 22. While proximal end 52 of compression spring 50 may alternatively be attached to the hub 20, such is not necessary in the embodiment shown to exert the required force on the wire 18. Compression spring 50 may also be integrally formed with the shank body of the wire 18. An embodiment in which the compression spring is integral with the wire and which does not use a wire hub is described below with reference to FIGS. 8 and 9. Proximal movement of occluding wire 18 is limited by the compression force of spring 50. The preferred force exerted by spring 50 on wire 18 is in the range of 0.25 pounds to 0.75 pounds and preferably is about 0.50 pounds. Accordingly, longitudinal movement of anchor 45 between distal and proximal positions is limited to approximately 0.59 inches. This is adequate to accommodate catheters of varying lengths.

Anchor 45 insures against detachment of occluding wire 18 from the hub 20 thus permitting easy removal of the wire from the longitudinal catheter body portion 11 while the wire is still assembled with hub 20. FIGS. 5 and 6 illustrate the assembly of occluding wire 18, compression spring 50 and hub portion 20 when hub 20 is uncoupled from catheter fitting 32 and the wire is withdrawn from the catheter body 11.

When wire hub 20 is assembled with the wire 18 so that anchor 45 is positioned in sections 60 and 48 of cavity 36, and with compression spring 50 secured at its distal end 51 to wire 18, the hub 20 may be coupled to the catheter hub 32 of body portion 11 to thus form the catheter assembly 10 of the invention. This arrangement allows for automatic adjustment of the occluding wire within catheter bodies of varying lengths due to variations in manufacturing tolerances of up to about +/−2.0 millimeters. This arrangement also allows for the catheter body 11 to flex or bend due to the catheter body engaging tortuous pathways during insertion, resulting in possible variations in the length that the occluding wire will engage the inside of walls 12 of the catheter body 11, while still automatically maintaining occluding wire 18 in the occluded distal position. Thus, the assembly of the present invention obviates the need for complicated, costly and difficult to use y-adapters and provides for automatic self-adjustment of the occluding wire in the catheter body to maintain its occluding position.

With reference to the embodiment illustrated in FIGS. 8 and 9, occluding wire 118 has a compression spring 150 either attached to its shaft, or as shown in this embodiment, wound directly from its shaft. The distal end of the wire 118 is the same as illustrated and described above having a coil spring 119 intended to protrude beyond the catheter distal end and a ball 138 intended to seat within the tapered zone 17 of the catheter. A proximal ball 140 is carried at the proximal end of wire 118 to provide a convenient means to grip the wire to facilitate removal of the wire from the catheter and to minimize chances of perforating sterile barrier gloves. In this embodiment occluding wire 118 is inserted into the catheter body through catheter hub 32. Spring 150 is positioned in catheter hub lumen 132. Lumen 132 has a tapered section 133 which will stop distal movement of the wire 118 as a result of distal end 151 of spring 150 engaging the tapered section 133. Spring 150 will be held in place within lumen 132 of catheter hub 32 by attachment of a male luer fitting 120 of a fluid source to the female port adapter 139. The proximal end 152 of spring 150 will abut against the distal end 163 of the male luer adapter 120. Spring 150 will exert the required force for urging wire 118 in the distal direction so that it will be biased into the occluding position, thus automatically adjusting the position of the wire 118. Male luer adapter 120 is attached to the female adapter 139 with screw threads 143 thereby capturing spring 150 within catheter hub lumen 132. Instead of spring 150, a screen, plate or other element larger than the diameter of the distal end of tapered section 133 may be carried by the wire 118 and captured within lumen 132 by male adapter 120 as a means for limiting the longitudinal movement of the wire 118. Occluding wire 118 can be withdrawn from the catheter body by disconnecting the male luer adapter 120 from the catheter hub 32 and grasping ball 140. The section 117 of the wire 118 which is proximal of the spring 151 will extend sufficiently beyond the proximal end of catheter hub 32 to allow adequate grasping of the ball 140 for withdrawal.

This invention has been described and illustrated in connection with a certain preferred embodiment which is illustrative of the principles of the invention. However, it should be understood that various modifications and changes may readily occur to those skilled in the art, and it is not intended to limit the invention to the constructions and operation of the embodiment shown and described herein. Accordingly, additional modifications and equivalents may be considered as falling within the scope of the invention as defined by the claims herein below.

The embodiments of the invention in which an exclusive property or privilege is claimed are defined as follows:

What is claimed is:

1. An occluding wire assembly for use in a catheter that has a hub and a lumen comprising:
   a fitting having a distal end and a proximal end, said distal end of said fitting adapted to be detachably connected to the hub of the catheter, said fitting having a main axis,
   a fluid passageway extending axially through said fitting so that fluid introduced into said passageway is delivered to the lumen of the catheter to which said occluding wire assembly is connected,
   an occluding wire extending axially from said fitting and having a proximal portion thereof contained within said fitting so that removal of said fitting from the hub of the catheter will withdraw said occluding wire from the catheter, and
   a spring attached to said proximal portion of said occluding wire and engaging a first surface of said fitting, said spring biasing said occluding wire in a distal direction when said spring engages said fitting.

2. The assembly of claim 1 wherein: said fitting has a cavity extending radially outward from said fluid passageway, said proximal portion of said occluding wire including an anchor element extending into said cavity to engage a second surface of said cavity during removal of said fitting from the hub of the catheter, movement of said occluding wire in a distal direction relative to paid fitting being limited by the abutting of said anchor element against said second surface of said cavity.

3. The occluding wire assembly of claim 2 wherein said first surface is a distally facing shoulder and wherein said spring has a proximal end which abuts against said shoulder when said fitting is fitted onto a catheter to provide said biasing of said occluding wire in a distal direction.

4. The occluding wire assembly of claim 1 wherein said first surface is a distally facing shoulder and wherein said spring has a proximal end which abuts against said shoulder when said fitting is fitted onto the catheter to provide said biasing of said occluding wire in a distal direction.

5. An occluding wire assembly for use in a catheter that has a hub and a lumen, comprising;
   a fitting having a distal end and a proximal end, said distal end of said fitting adapted to be detachably connected to the hub of the catheter, said fitting having a main axis,
   a fluid passageway extending axially through said fitting so that fluid introduced into said passageway is delivered to the lumen of the catheter to which said occluding wire assembly is connected,
   an occluding wire extending axially from said fitting and having a proximal portion thereof contained within said fitting,
   a spring formed in the body of said occluding wire,
   said fitting having a distally facing wall and said spring having a proximal end which abuts against said wall when said fitting is fitted onto the hub of a catheter to bias said occluding wire in a distal direction.

6. The occluding wire assembly of claim 5 wherein: said occluding wire has a proximal element to facilitate manual removal of said wire from the catheter when said fitting has been removed.

\* \* \* \* \*